US009089819B2

(12) United States Patent
Walavalkar et al.

(10) Patent No.: US 9,089,819 B2
(45) Date of Patent: Jul. 28, 2015

(54) PARTICULATE NANOSORTING STACK

(75) Inventors: Sameer Walavalkar, Los Angeles, CA (US); Aditya Rajagopal, Irvine, CA (US); Axel Scherer, Woodstock, VT (US); Thomas A. Tombrello, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 592 days.

(21) Appl. No.: 13/250,575

(22) Filed: Sep. 30, 2011

(65) Prior Publication Data

US 2012/0080361 A1 Apr. 5, 2012

Related U.S. Application Data

(60) Provisional application No. 61/388,342, filed on Sep. 30, 2010, provisional application No. 61/405,019, filed on Oct. 20, 2010.

(51) Int. Cl.
*B01D 71/00* (2006.01)
*B01D 71/02* (2006.01)
*B01D 67/00* (2006.01)
*B07B 1/00* (2006.01)
*B82Y 40/00* (2011.01)
*B01D 61/02* (2006.01)
*B01D 61/14* (2006.01)

(52) U.S. Cl.
CPC .......... *B01D 71/027* (2013.01); *B01D 67/0062* (2013.01); *B07B 1/00* (2013.01); *B82Y 40/00* (2013.01); *B01D 61/027* (2013.01); *B01D 61/145* (2013.01)

(58) Field of Classification Search
CPC .... B07B 1/4663; B01D 61/18; B01D 61/142; B01D 67/0023; B01D 67/0062; B01D 71/027
USPC .......... 209/311, 315, 316, 392, 397; 977/707, 977/712, 845
See application file for complete search history.

(56) References Cited

U.S. PATENT DOCUMENTS

| | | | |
|---|---|---|---|
| 7,279,134 B2 * | 10/2007 | Chan et al. .................... | 422/503 |
| 7,592,255 B2 | 9/2009 | Kuekes et al. | |
| 8,518,276 B2 * | 8/2013 | Striemer et al. ................ | 216/2 |
| 8,622,223 B2 * | 1/2014 | Zhang et al. ............. | 210/500.21 |
| 8,906,234 B2 * | 12/2014 | Yamamoto et al. ........ | 210/321.6 |
| 2003/0116531 A1 | 6/2003 | Kamins et al. | |

(Continued)

FOREIGN PATENT DOCUMENTS

JP   2005-246340 A   9/2005

OTHER PUBLICATIONS

Henry et al., "Alumina etch masks for fabrication of high-aspect-ratio silicon micropillars and nanopillars", *Nanotechnology* vol. 20 (2009).

(Continued)

*Primary Examiner* — Joseph C Rodriguez
(74) *Attorney, Agent, or Firm* — Knobbe, Martens, Olson & Bear LLP

(57) ABSTRACT

Methods and devices for isolating and sorting nanoparticles are disclosed herein. Nanopores of a desired size can be formed in silicon dioxide membranes and used as filters to separate nanoparticles. Devices are also provided herein for sorting nanoparticles with multiple filters having various sized nanopores.

28 Claims, 12 Drawing Sheets

(56) References Cited

U.S. PATENT DOCUMENTS

| | | |
|---|---|---|
| 2006/0003458 A1 | 1/2006 | Golovchenko et al. |
| 2007/0190542 A1 | 8/2007 | Ling et al. |
| 2008/0187915 A1 | 8/2008 | Polonsky et al. |
| 2010/0066348 A1 | 3/2010 | Merz et al. |
| 2010/0181288 A1 | 7/2010 | Tang et al. |
| 2010/0213579 A1 | 8/2010 | Henry et al. |
| 2010/0322825 A1* | 12/2010 | Yamakawa et al. ........ 422/82.05 |
| 2012/0097610 A1* | 4/2012 | Zheng et al. .................. 210/650 |
| 2012/0205306 A1* | 8/2012 | Reich et al. ................... 210/519 |
| 2013/0306549 A1* | 11/2013 | Tringe et al. ............. 210/500.22 |
| 2014/0021133 A1* | 1/2014 | Siwy et al. .................... 210/650 |

OTHER PUBLICATIONS

Liu et al., "Self-limiting oxidation for fabricating sub-5 nm silicon nanowires", *Appl. Phys. Lett American Institute of Physics* vol. 64 No. 11, pp. 1383-1385.

U.S. Appl. No. 13/248,994, filed Sep. 29, 2011.

International Search Report dated May 2, 2012 in corresponding International Patent Application No. PCT/US2011/054366.

Sigalov et al. "Detection of DNA Sequences using an Alternating Electric Field in a Nanopore Capacitor," Dec. 11, 2007, Nano Letters, vol. 8, No. 1, pp. 56-63.

13248991-425129-EICSearch (USPTO in-house SITC search), Jul. 8, 2013.

\* cited by examiner

PARTICULATE NANOSORTING STACK

CROSS-REFERENCE TO RELATED APPLICATIONS

This application claims priority under 35 U.S.C. §119(e) to U.S. Provisional Patent Application Ser. No. 61/405,019, entitled MEASURING DNA POLYMERASES USING IN-PLANE SELF ALIGNED CAPACITORS, filed Oct. 20, 2010 and U.S. Provisional Patent Application Ser. No. 61/388,342, entitled SEQUENCING OF SINGLE-STRANDED DNA BY MEANS OF SMALL-SIGNAL CAPACITANCE MEASUREMENT, filed Sep. 30, 2010, the full disclosures of which are hereby incorporated by reference.

STATEMENT REGARDING FEDERALLY SPONSORED R&D

This invention was made with government support under W911NF-07-1-0277 awarded by ARO-US Army Robert Morris Acquisition Center. The government has certain rights in the invention.

BACKGROUND OF THE INVENTION

1. Field of the Invention

The invention relates generally to filters comprising nanopores and methods of filtering nanoparticles.

2. Description of the Related Art

Devices and methods for filtering nanoparticles can be used in a variety contexts. For example, over the past decade there has been much interest in the isolation and study of exosomes and other biological particles (vesicles, viruses, DNA, etc.) with nanometer sizes. Due in part to the unavailability of effective nanometer scale filtration options, current techniques to isolate such particles rely on chemical techniques or the use of ultra high speed (greater than 100,000 g) centrifugation. Such techniques are non-specific and physically damaging (such as centrifugation) or must be tailored to each particle (such as chemical or antibody binding approaches). In addition to biological nanoparticles, improved nanometer scale filters will find use in many other contexts where separation of particles by size is desired. These include, for example, protein filtration, dialysis, water filtration, as well as many industrial contexts.

SUMMARY OF THE INVENTION

Methods and apparatuses are provided herein for making and using filters comprising nanopores. The filters find use, for example, in sorting particles based on size.

According to some embodiments, a filter comprising two or more nanopores, wherein each of the nanopores has a diameter of about 5 nm or less is provided. In some embodiments the nanopores have a diameter of 2 nm or less. The nanopores are open to a top and bottom of the substrate, thus allowing fluid and particles smaller than the nanopores to pass through.

According to some embodiments, devices for sorting particles are provided. The devices comprise a first filter comprising two or more nanopores each having a first diameter; a second filter comprising two or more nanopores each having a second diameter, wherein the first diameter is different than the second diameter, and wherein the first diameter or the second diameter is about 5 nm or less. In some embodiments the nanopores have a diameter of 2 nm or less. The first and second filters are arranged in the device to provide a flow path from the first filter to the second filter. The first and second filter may be fluidly connected by a spacer that provides a flow path from the first filter to the second filter. For example, an elastomer layer may be present between the first and second filter. In some embodiments, the device further comprises a first microfluidic device configured to direct a sample to the first filter and a second microfluidic device located after the second filter and configured to collect the sample and particles smaller than any of the pores in the filters.

According to some embodiments, methods for forming devices are provided. The methods include providing a silicon substrate having a top side and a bottom side, forming a first nanopillar on the substrate, oxidizing the nanopillar to form a SiO2 layer around a silicon core, removing a portion of the nanopillar from the substrate to expose the silicon core, and selectively removing the silicon core by etching to form a pore in the substrate.

In some embodiments, an oxide layer is provided on the bottom side of the substrate. The oxide layer is etched directly below the first nanopillar to expose the silicon substrate, and the exposed silicon substrate is etched, thereby removing the core and forming a nanopore through the substrate.

According to some embodiments, methods of separating particles from a sample are provided. The methods include flowing the sample comprising the particles through a first filter, wherein the first filter comprises two or more nanopores with a diameter smaller than the particles to be separated from the sample, and wherein the nanopores are formed in a silicon dioxide layer and have a diameter less than about 10 nm. In some embodiments, the nanopores have a diameter of about 5 nm or less. In some embodiments, the nanopores have a diameter of about 2 nm or less.

According to some embodiments, methods of sorting nanoparticles by size are provided. The methods include flowing a sample comprising two or more nanoparticles through a first filter, wherein the first filter comprises two or more nanopores formed in a silicon dioxide layer, each nanopore having a first diameter and subsequently flowing the sample through a second filter, wherein the second filter comprises two or more nanopores formed in a silicon dioxide layer, each nanopore having a second diameter smaller than the first diameter. The two or more nanoparticles comprise at least one first nanoparticle with a third diameter larger than the first diameter and at least one second nanoparticle with a fourth diameter larger than the second diameter. The second diameter may be equal to or less than about 5 nm or less than about 2 nm. The nanopores may be formed in a silicon dioxide layer on a substrate. The sample may be flowed with the aid of a pressure fluid. In some embodiments, the method further comprises extracting the sorted particles.

DETAILED DESCRIPTION

Disclosed herein are devices comprising nanopores, as well as methods and apparatuses for forming and using the devices. The devices can be used, for example, as filters, for example for filtering and/or sorting nanoparticles based on size. The devices can be formed using standard techniques developed in the semiconductor industry. In some embodiments, nanometer scale pores are formed in a silicon dioxide layer and can be used to separate particles based on size. The pores are in fluid communication with both the top and bottom sides of the silicon dioxide layer. Stacks made of several filters allow for sorting a mixture of particles by size.

In some embodiments, particles of a particular size are separated from a sample by passing the sample through a filter comprising an array of nanopores. In some embodiments all or substantially all of the nanopores are of approximately the same diameter. In some embodiments a mixture of particles can be sorted by size by passing the mixture through a series of filters, each having an array of nanopores of a particular size.

Methods are also disclosed herein for forming the nanopores on substrates. In some embodiments, the nanopores can be sized to allow only nanoparticles of a particular size through the substrate. For example, nanopores can be sized such that only particles less than 5 nm, 4 nm, 3 nm, 2 nm, or 1 nm can pass through the substrate.

While described primarily herein in relation to their use as filters, the skilled artisan will appreciate that the disclosed devices comprising nanopores can be used in a wide variety of other contexts, such as substrates for the growth of cells in culture.

Nanoparticle Filters

Figure 10A:
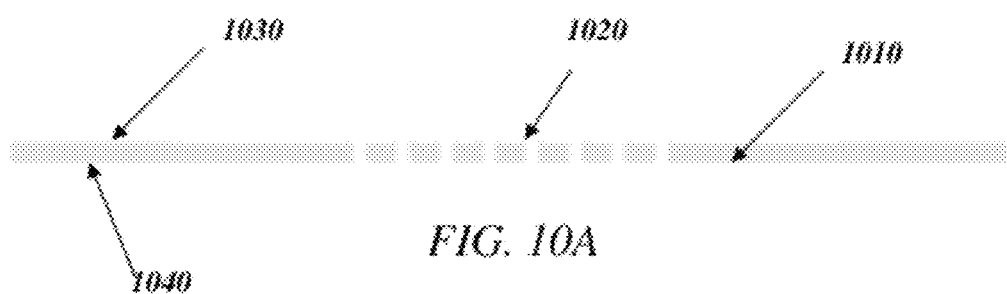
FIG. 10A is an illustrative embodiment of a filter according to one embodiment.
Figure 10B:
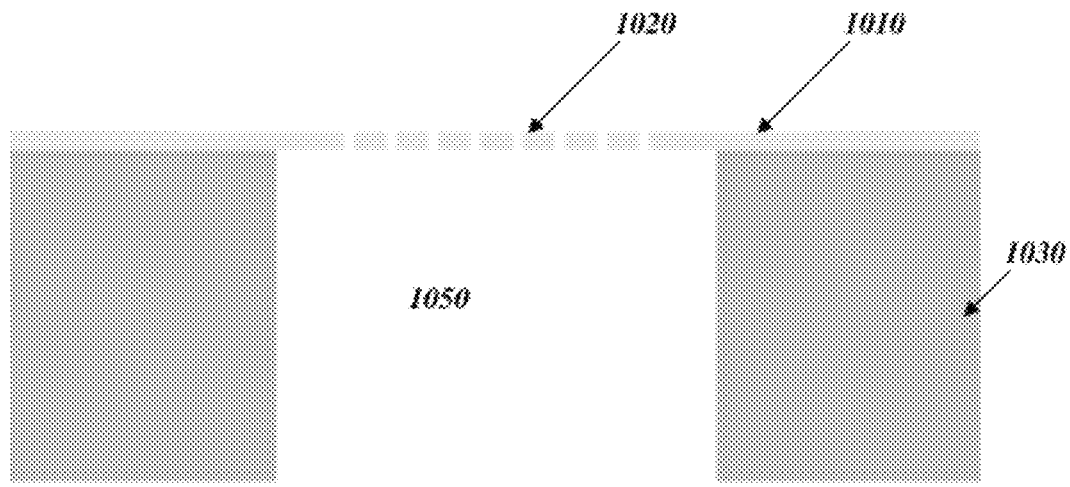
FIG. 10B is an illustrative embodiment of a filter according to one embodiment.

Devices for filtering particles comprise a substrate and at least one nanopore on the substrate. In some embodiments a filter comprising nanopores is prepared from a silicon substrate. As described below, during the process of forming the nanopores, the substrate may be oxidized and a portion of the remaining silicon (if any) may be removed. In some embodiments, all of the remaining silicon is removed, leaving a silicon dioxide membrane comprising nanopores. Thus, in some embodiments the filter may comprise, for example, a silicon dioxide membrane. For example, as illustrated in FIG. 10A, the filter may comprise a silicon dioxide membrane 1010 with at least one nanopore 1020. As illustrated, the nanopores are in fluid communication with a top side 1030 and a bottom side 1040 of the membrane. However, in some embodiments the filter may comprise a variety of materials, such as silicon and silicon dioxide. For example, as illustrated in FIG. 10B, the filter may comprise a silicon dioxide layer 1010, at least one nanopore 1020 and a silicon layer 1030. As illustrated, the nanopores are in fluid communication with a top side 1030 of the substrate and an internal cavity in the substrate 1050. In some embodiments the nanopores are formed only in a silicon dioxide layer. In other embodiments, the nanopores are formed in a silicon dioxide layer and extend through an additional layer, such as an underlying or overlying silicon layer.

In addition, the filters comprise other materials and structures. For example, a filter may comprise integrated microelectronic devices. In some embodiments the filter may comprise metal layers that may serve, for example, as sensors for detecting the passage of nanoparticles through the pores on the substrate. In some embodiments, a filter may comprise additional physical features. For example, in some embodiments a filter may comprise materials that serve to physically separate areas of the filter. For example, the filter may comprise one or more physical barriers that separate areas of the filter comprising arrays of nanopores of different sizes. In some embodiments filters may comprise internal flowpaths in fluid communication with one or more nanopores, wherein the pathways are arranged to allow a liquid to flow to a desired portion of the filter. In some embodiments a flowpath may be in fluid communication with one or more of the nanopores.

In some embodiments the nanopores have a diameter equal to or less than about 10, 9, 8, 7, 6, 5, 4, 3, 2 or 1 nm. In some embodiments nanopores have a diameter of about 1, 2, 3, 4, 5, 6, or 7 nm. Diameter, as used herein, refers to the average or median width of the pore. In some particular embodiments, filters comprising nanopores of about 2 nm or less are provided.

The size of the nanopores is preferably selected to allow the passage of one or more nanoparticles of a particular size, while excluding larger particles. In some embodiments, the diameter of the at least one nanopore of a filter is about 2 nm or less. In some embodiments, the nanopore can have an average or median diameter of about 2 nm or less. In some embodiments, the nanopore can have a diameter of less than about 1 nm, 2 nm, 3 nm, or 4 nm.

In some embodiments, filters comprise two or more nanopores, where each nanopore has the same size. For example, a filter may comprise 2, 3, 4, 5, 10, 100, 1000, 10000, 100000, 1000000 or more nanopores of the same size. In some embodiments all of the nanopores on a filter are the same size.

As discussed in more detail below, in some embodiments filters comprising one or more arrays of nanopores are provided. The arrays may comprise, for example, 2, 3, 4, 5, 10, 100, 1000, 10000, 100000, 1000000 or more nanopores. In some embodiments the nanopores are regularly spaced in the arrays. In some embodiments all of the nanopores in an array are the same size. In some embodiments the nanopores in an array may have differing sizes.

In some embodiments, the nanopores are arranged in a regular pattern on the filter.

The distance between nanopores can be selected as desired for a given application. In some embodiments, the distance between nanopores can be about 100 nm to 300 nm from center to center. In some embodiments, the distance between nanopores can be about 300 nm to 500 nm from center to center. In some embodiments, the distance between nanopores can be about 500 nm to 1 micron from center to center. In some embodiments, the distance between nanopores can be about 150 nm from center to center.

In some embodiments, all or substantially all of the nanopores on the substrate are approximately the same diameter. For example, a substrate may comprise two or more nanopores, where each nanopore has approximately the same diameter. In some embodiments, a filter comprises two or more nanopores of about 2 nm in diameter.

In other embodiments, a single substrate may comprise nanopores of different sizes. In some embodiments, nanopores of a particular size are grouped together on the substrate. For example, a first portion of a substrate may comprise nanopores of a first diameter and a second portion of a substrate may comprise nanopores of a second diameter, wherein the second diameter is different from the first diameter. The areas of different diameter nanopores may be separated from each other, for example to enable the passage of a sample through a single size of nanopores. In some embodiments the areas of different diameter nanopores are separated spatially. In some embodiments the areas of different diameters are separated physically, for example by a physical barrier.

As mentioned above, in some embodiments, multiple regions of nanopores can be integrated on a single substrate. For example, multiple nanopores, for example multiple arrays of nanopores, can be provided in different, physically separated areas of a single substrate. See, for example, the device illustrated in FIG. 11 and described in more detail below. In this way, multiple samples can be isolated or sorted on the same substrate using multiple individual devices. Thus, many nanoparticle samples can be sorted simultaneously in parallel using a single substrate comprising an array of filtering devices. Alternatively, a single sample can be passed through multiple sized nanopores by being flowed through different regions of a substrate (as in the device illustrated in FIG. 11).

Figure 7:
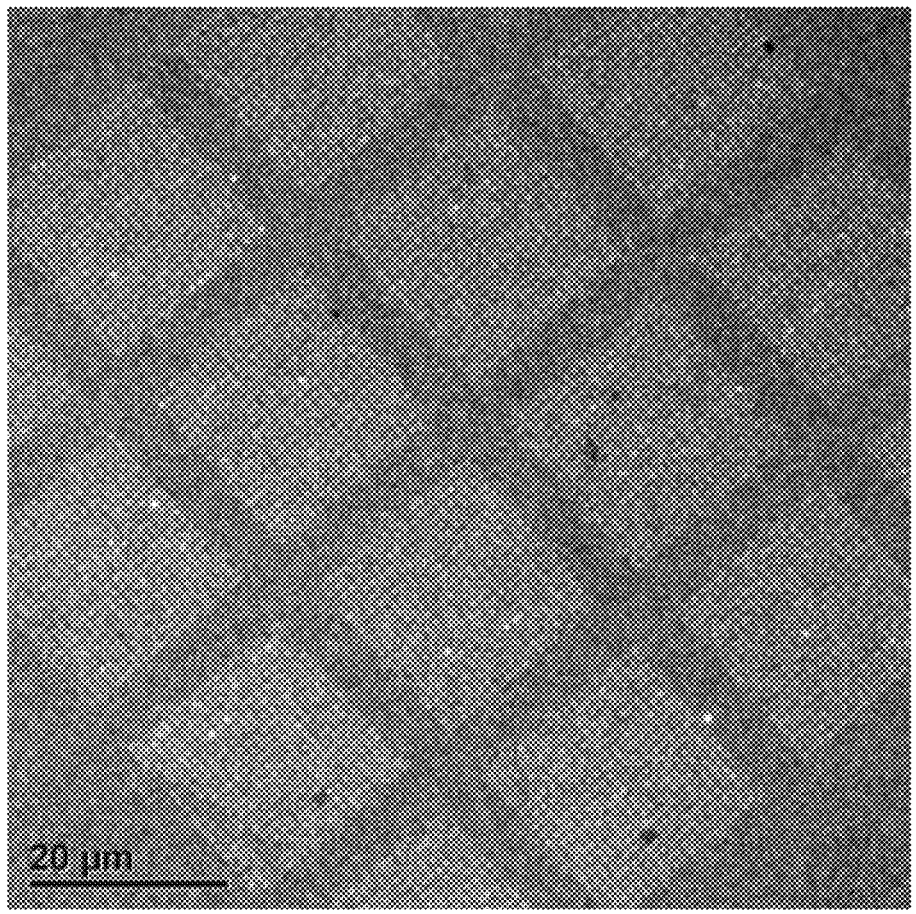
FIG. 7 shows an image of an array of silicon nanopores formed according to one embodiment.
Figure 8:
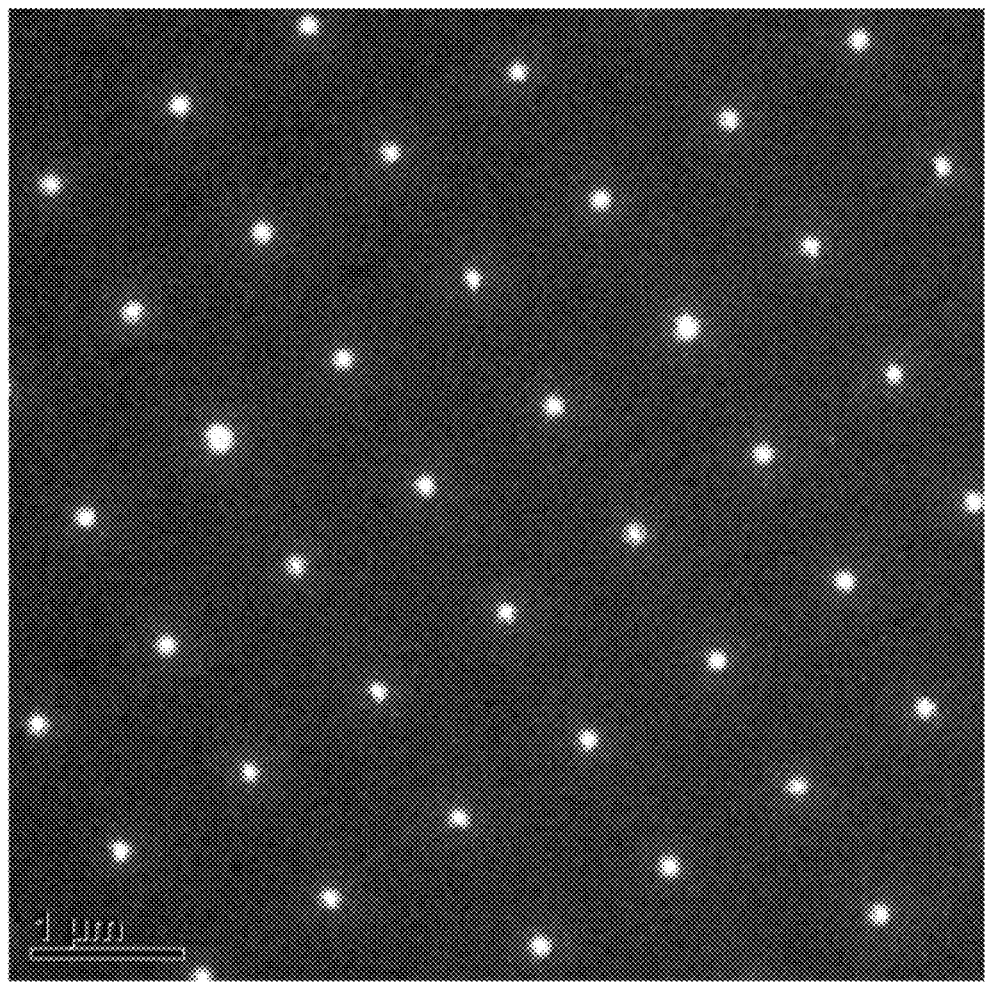
FIG. 8 shows an image of an array of silicon nanopores formed according to one embodiment.
Figure 9:
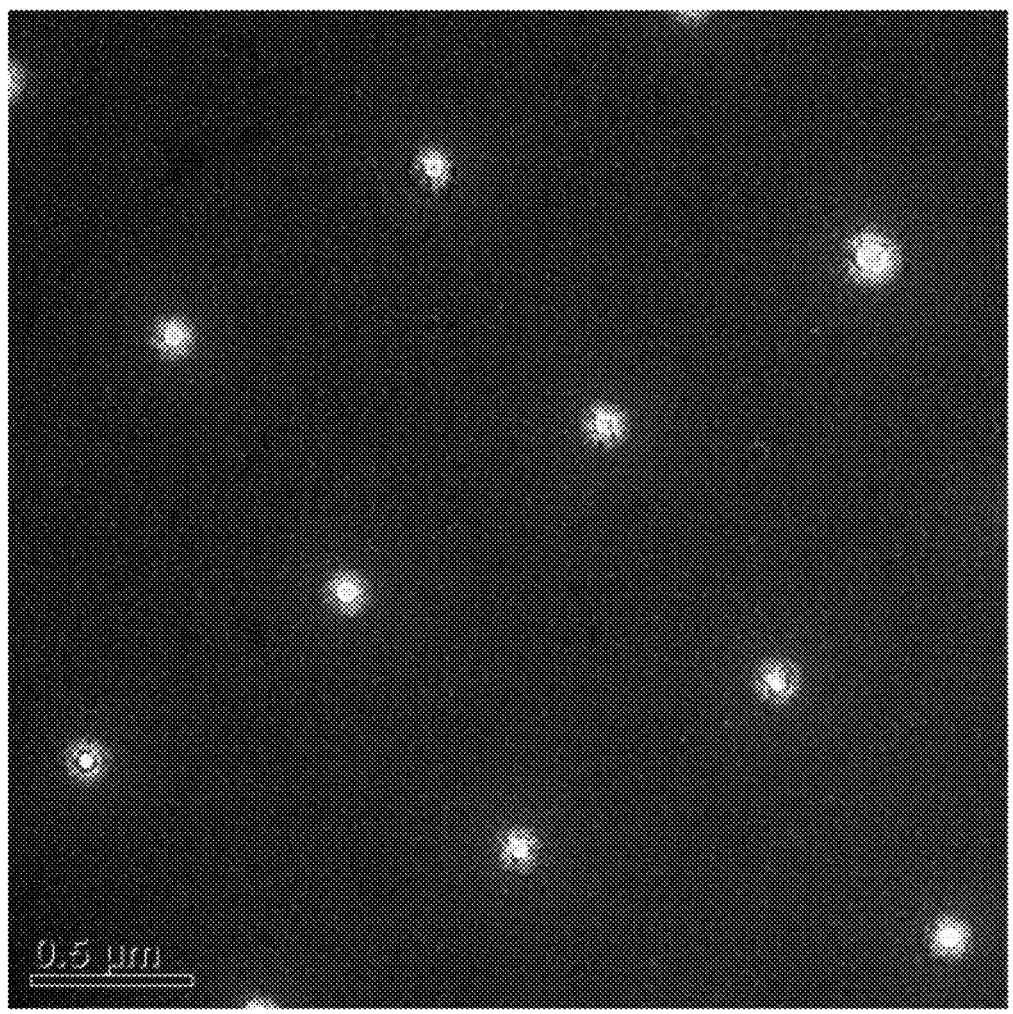
FIG. 9 shows an image of an array of silicon nanopores formed according to one embodiment.

Exemplary arrays of nanopores are illustrated in FIGS. 7, 8 and 9.

A filter comprising nanopores may have any desired thickness. The thickness can be selected based on the particular use and the desired structure of the filter. In some embodiments, the filter has a total thickness of about 300 microns. In some embodiments the filter has a total thickness of about 100 to 500 microns or more. However, in some embodiments the filter may have a thickness of about 10 to about 300 nm, for example if the filter comprises only a silicon dioxide membrane containing the nanopores. In some embodiments the thickness of the silicon dioxide layer comprising the nanopores is about 10 to 300 nm, or 10 to about 100 nm. In some embodiments, a filter comprising a silicon dioxide layer with nanopores with a diameter or 2 nm or less may have a silicon dioxide layer thickness of about 10 to 100 nm. In some embodiments, a filter may have a silicon dioxide layer thickness of about 300 nm.

Nanoparticle Sorting Devices

One or more filters comprising nanopores may be used to separate particles by size. In some embodiments, a single filter may be used to separate particles of a particular size or sizes from a sample. For example, a single filter may comprise nanopores of a single desired size. As discussed in more detail below, a sample, typically a liquid comprising one or more particles, is applied to the filter and particles smaller than the diameter of the nanopores are able to pass through the filter. Particles that pass through the filter, and thus that are smaller than the nanopore diameter, may be collected. In addition, particles that are retained and thus that are of a larger size than the nanopore diameter may also be collected.

In other embodiments a filter may comprise nanonpores of a two or more sizes. For example, a single filter device may comprise nanopores of two, three, four, five or more different sizes. The different sized nanopores may be located in specific regions of the substrate. For example, in the device illustrated in FIG. 11, a first portion of the substrate 1110 may comprise only nanopores of a first size, while a second portion 1120 comprises nanopores of a second size. A third area 1130 may comprise nanopores of a different size from the first two areas 1110 and 1120, etc. . . . . .

In other embodiments, devices for filtering nanoparticles and/or sorting nanoparticles comprise two or more filters. Such a device may be referred to as a filter stack, or simply a stack. In some embodiments, the device comprises multiple filters, arranged such that a sample passes sequentially through each filter. For example, the device may comprise a flow path that allows a sample, such as a liquid or other fluid sample, to pass through a series of two or more filters in sequence. The stack may include a first filter and a second filter separated by a spacer layer. The spacer layer may provide a flow path that allows for at least a portion of a sample that has passed through nanopores in the first filter to flow to the second filter. In addition, the spacer layer may provide access to the region between the first and second filter, such that material (such as particles) that has flowed through the nanopores of the first filter and not through the second filter can be collected. Additional spacer layers and filters may be used between other filter sets; for example three, four, five, six, seven, eight, nine, ten or more filters may be utilized, with a spacer layer between the first and second filter, second and third filter etc. . . . . . Thus, in some embodiments each filter is separated from filters above by a spacer layer.

A microfluidic device, such as a chamber formed of an elastomer, may be disposed above the first filter to provide a means of providing the sample to be filtered to the first filter. For example, the microfluidic device may comprise a chamber that is pierceable by a needle, such that a fluid sample can be injected into the chamber. The chamber may be in fluid contact with the nanopores on the first filter, such that a flow path is created from the microfluidic device to the first filter. In addition, a second microfluidic device may be disposed under the last filter in a stack, and in fluid communication with at least a portion of the nanopores in the last filter, such that fluid flowing through the last filter is collected and can be removed.

In some embodiments, each filter in a device comprising multiple filters may comprise different size nanopores from other filters in the device. In other embodiments, two or more filters in a stack may comprise the same size nanopores.

In some embodiments, a flow path is created such that a fluid sample can be flowed through each of two or more filters sequentially, where each filter has a smaller nanopore size than the previous filter. Portions of the sample retained at each filter (for example because the particles are two large to pass through the nanopores of the subsequent filter), can be removed.

In other embodiments, a device may comprise multiple filters but be arranged such that multiple samples pass through different filters simultaneously.

Figure 1:
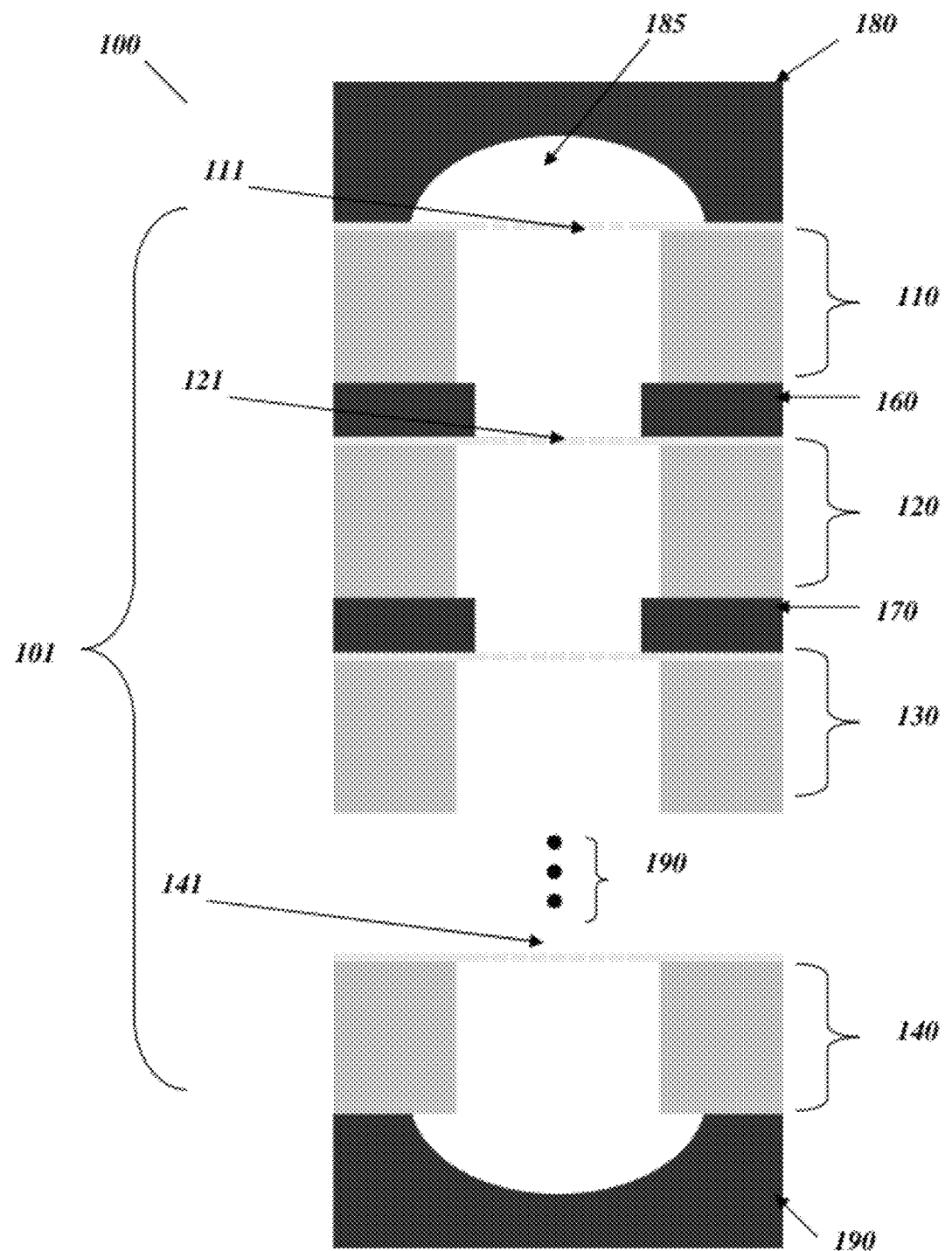
FIG. 1 is an illustrative embodiment of a device for sorting particles.

Referring to FIG. 1, in some embodiments a stack device for filtering particles 100 comprises: a first filter 110 comprising at least one nanopore 111 and a second filter 120 comprising at least one nanopore 121. The first filter 110 may also be referred to as the top filter, and is typically the first filter that a sample passing through the device will encounter.

In some embodiments, a diameter of the at least one nanopore 121 of the second filter is different than a diameter of the at least one nanopore 111 of the first filter. In some embodiments the nanopores of the second filter 121 are smaller than the nanopores of the first filter 111.

In some embodiments a filtration device comprises at least one spacer layer 160 separating the first filter 110 and the second filter 120. In some embodiments the spacer layer 160 may serve not only to separate the filters, but also to provide a flow path to the second filter 120. That is, the spacer layer 160 may contain and direct the sample to the second filter 120. The spacer layer 160 may be, for example, an elastomer layer. In some embodiments the layer 160 is formed from PDMS. This layer 160 may be configured to allow at least a portion of a sample that has passed through the overlying layer to be removed during or after filtration. For example, nanoparticles that were able to pass through the first filter 110 but not the second filter 120 may be removed. In some embodiments the spacer layer 160 may be penetrable, for example by a needle, to allow removal of material from between filters. It may also allow addition of material to the space between filters, such as additional liquid or reagents. In some embodiments the spacer layer 160 is between and adjacent to the first filter 110 and the second filter 120, or between any two other filters in a stack.

The device 100 may comprise additional filters. The illustrated device comprises a third filter 130 and a bottom filter 140. As represented by the dashed line 190, additional sets of filters and spacers may be located between filter 130 and the bottom filter 140. The filters may be arranged as illustrated such that a sample passes sequentially through the first 110, second 120, third 130 and bottom 140 filters, as well as through any intervening filters between filter 130 and bottom filter 140. That is, there may be a flow path for the sample between all of the filters in the stack.

In some embodiments, each of the filters may comprise different size nanopores such that as a sample moves through the series of filters, particles of different sizes may be separated and collected. In some embodiments a sample is passed through filters having sequentially smaller nanopores. Thus, in some embodiments the diameter of the at least one nanopore 121 of the second filter is different than the diameter of the at least one nanopore 111 of the first filter. Similarly, the diameter of the nanopores of each filter of the sequence of filters may be different than the diameter of the nanopores of the other filters. In some embodiments the filters have sequentially smaller pore sizes. For example, the filters 110, 120, 130, and 140 may be stacked from largest pore size to smallest pore size. The pore sizes may be selected such that a mixture of different size nanoparticles is separated by size, wherein each size of particle may be collected where it encounters a filter with nanopores smaller than that particle size.

A spacer layer 160 may be an elastomer layer between the first filter 110 and the second filter 120. In some embodiments, an elastomer layer separates each of the filters 110, 120, 130, and 140 from the filter above. For example, an elastomer layer 170 may be located between the second filter 120 and the third filter 130. An elastomer layer may also be located between the third filter 130 and the fourth filter 140, and any additional pairs of adjacent filters.

In some embodiments, the diameter of the nanopore of at least one of the filters is about 7 nm, 6 nm, 5 nm, 4 nm, 3 nm, 2 nm, 1 nm or less. In some embodiments, an average or median diameter of at least one nanopore of the last filter in a filter stack (here nanopore 141) is about 2 nm, 1 nm or less.

In some embodiments, the diameter of the nanopore 121 of the second filter 120 is smaller than a diameter of the nanopore 111 of the first filter 110.

Figure 2:
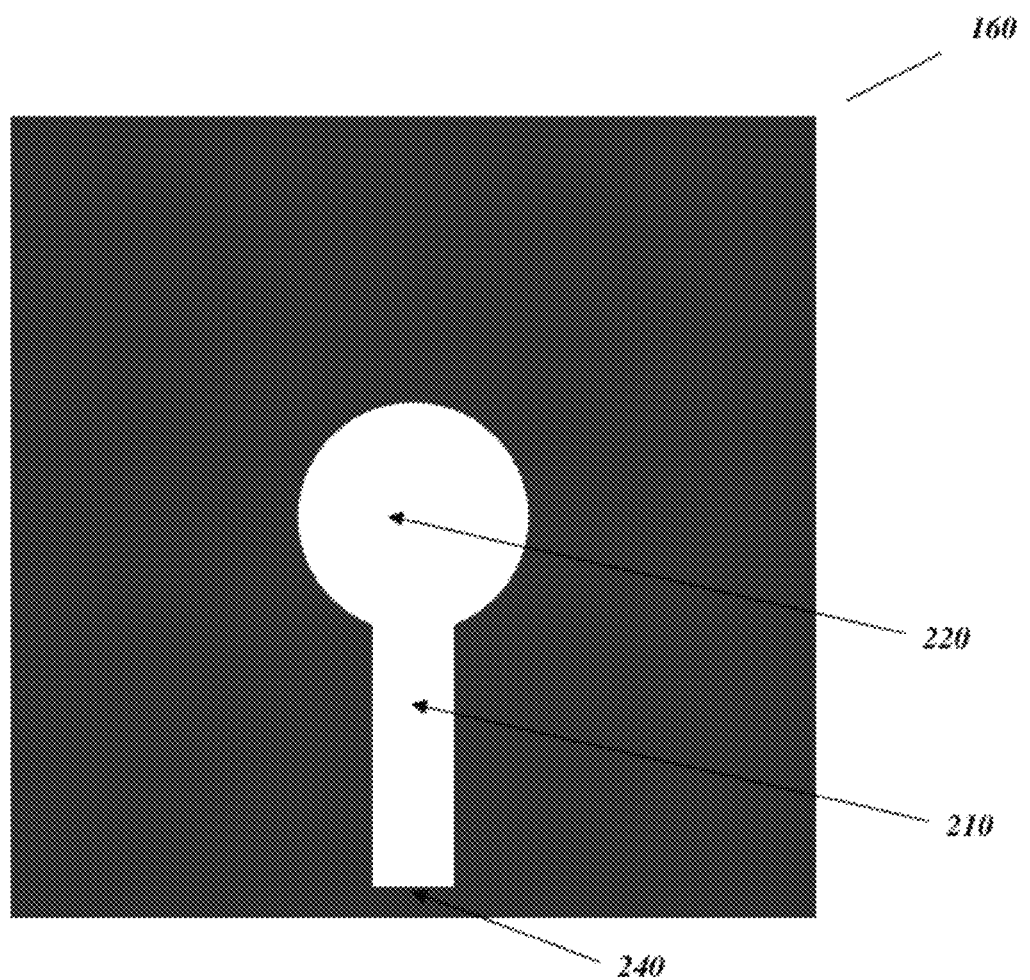
FIG. 2 is an illustrative embodiment of a spacer layer in the device of FIG. 1.

FIG. 2 illustrates one embodiment of a spacer layer 160. In some embodiments, the spacer layer comprises a hole 220 and a channel 210. In other embodiments the spacer does not comprise a channel. The hole 220 is located under at least a portion of the nanopores of the overlying filter and over at least a portion of the nanopores on the underlying layer, providing a flow path from the overlying filter to the underlying filter such that a sample passing through the overlying filter is contained and contacts the nanopores of the underlying filter. Channel 210 may be used to add or remove material from the space between the filters. For example, particles can be removed that have passed through the overlying filter but not through the underlying filter. In addition, fluid may be provided through the channel to assist flow of the sample through the filters. The channel 210 may approach an outer edge of the layer 160 leaving a thin membrane 240. In some embodiments the membrane 240 may be about 2 mm or less. In some embodiments, the membrane 240 is configured to be punctured with a needle, such as a microfluidics needle.

In some embodiments, the spacer layer 160 is an elastomer layer made from PDMS. In some embodiments, the elastomer layer is formed by molding a UV activatable polymer. In some embodiments, the elastomer layer is made from syphil, or SQ-8. Other materials for forming the elastomer layer and method of manufacturing the layer will be apparent to the skilled artisan.

Referring again to FIG. 1, in some embodiments, the device 100 may further comprise a first microfluidic device 180 overlying the stack. The first microfluidic device 180 may be, for example, configured to insert a carrier fluid and/or sample into the device such that it contacts the nanopores of the first filter in the stack. In some embodiments the device 180 is an elastomeric material such that a needle can be used to inject a sample into the space 185 above the first filter 110. The device 185 may be, for example, a molded elastomeric material such as PDMS.

Figure 3:
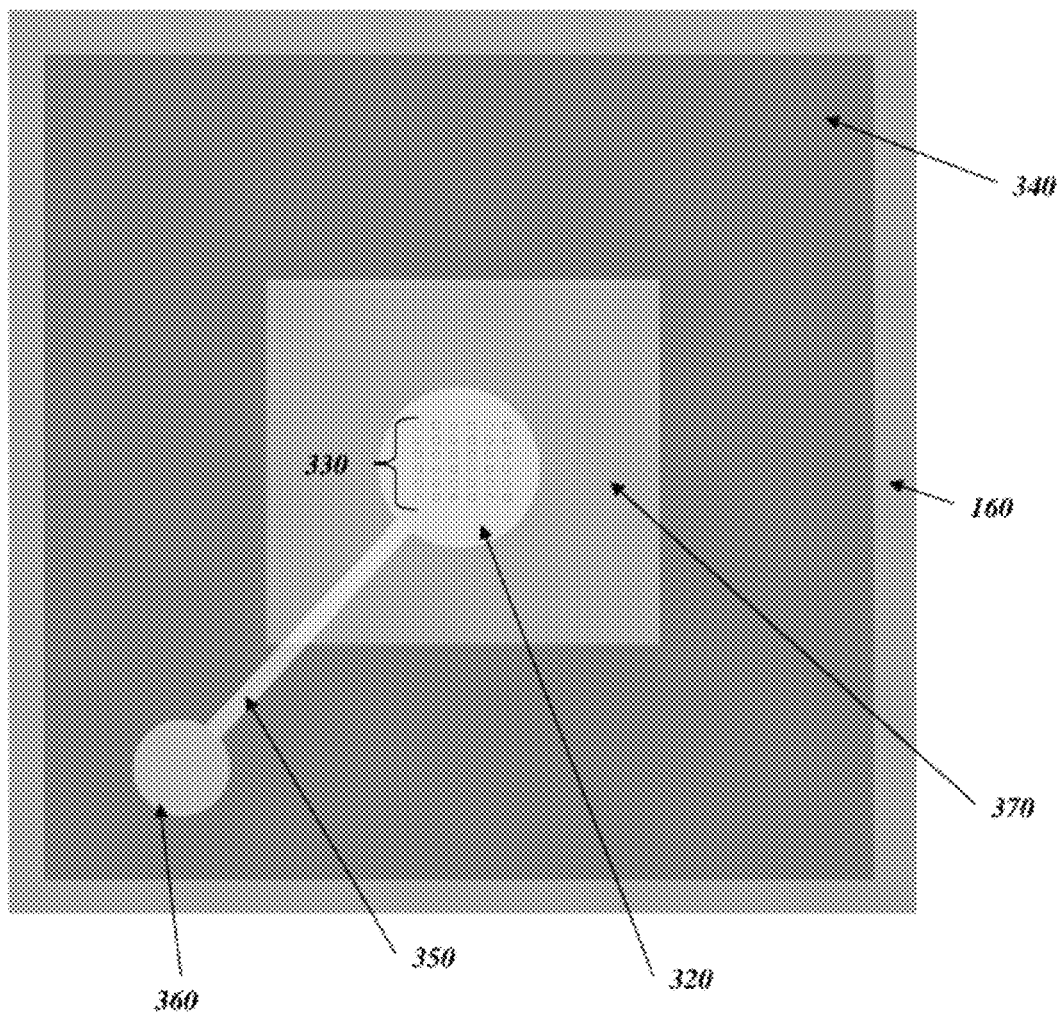
FIG. 3 is a top view of the device of FIG. 1.

FIG. 3 illustrates a cut-away view of a microfluidic device 340. Here, a hole 320 is illustrated over an array of nanopores 330 on the underlying filter 340. The channel 350 is in fluid communication with the hole 320, and in turn with space 370 (corresponding to space 185 in FIG. 1). Addition or removal of a sample and/or other material to the space 370 through hole 320 can thus be achieved by providing the sample to channel 350. Material may be introduced into the channel through a port 360. The port 360 may be open to the environment. In other embodiments the port 360 may be accessible, for example by penetrating an overlying membrane with a needle.

In some embodiments, the device further comprises a second microfluidic device 190 located at the bottom of the stack, below the final filter 140. The second microfluidic device 190 may be configured to collect the sample and particles that have passed through all of the filters of the stack 100. In some embodiments, the sample that is collected in the microfluidic device 190 will comprise only particles that are smaller than any of the pores in the filters.

In other embodiments a device may comprise a single filter (formed from one substrate) with nanonpores of two or more sizes. For example, a filter may comprise two physically separated filtration regions and the sample may be contacted with a first filtration region of the filter comprising nanopores of a first size, and subsequently contacted with a second filtration region of the filter having nanopores of a second size. For example, two or more regions having different sized nanopores may be in series in a single flowpath on a substrate. In this way, a single filter can be used to sort particles of various sizes.

Figure 11:
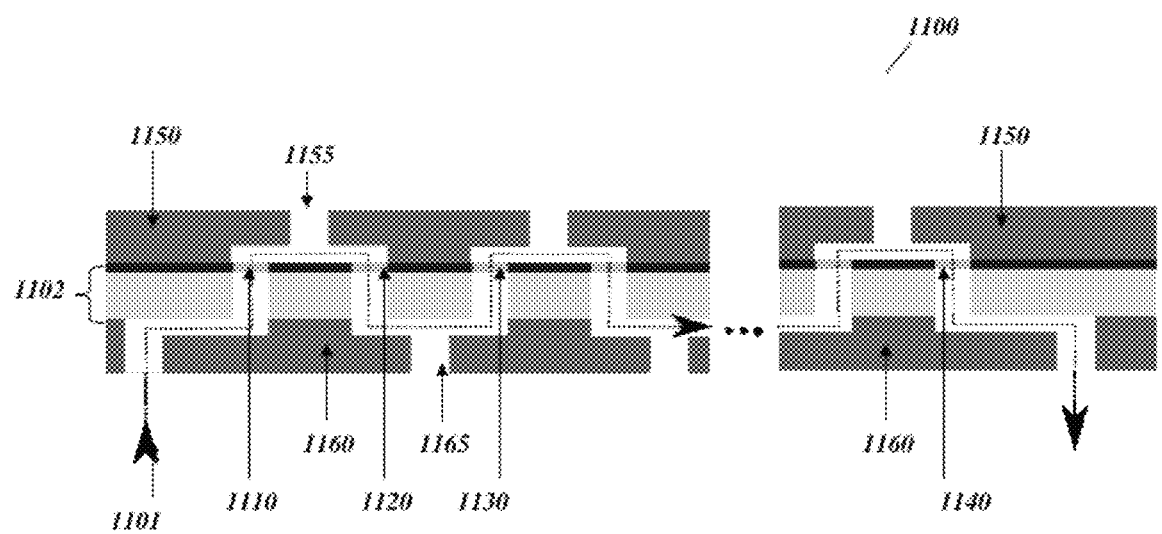
FIG. 11 illustrates a cross-sectional view of a sorting device according to one embodiment.

FIG. 11 illustrates a cross-sectional view of a sorting device with a series of filtration regions on a single substrate according to one embodiment. The illustrated device 1100 comprises a single substrate 1102, a first filtration region 1110, and a second filtration region 1120.

The device 1100 may comprise additional filtration regions. The illustrated device comprises a third filtration region 1130 and a last filtration region 1140. As represented by the dashed line, additional filtration regions may be located between filtration region 1130 and the final filtration region 1140. The filtration regions may be arranged as illustrated such that the filters are in series in a single flow path (dotted line 1101 with arrows indicating direction of flow). That is, each filtration region is in fluid communication with the next filtration region, and a sample may flow through each of the filtration regions in order. The device may thus be arranged as illustrated such that a sample passes sequentially through the first 1110, second 1120, third 1130 and last 1140 filtration regions, as well as through any intervening filtration regions between filtration region 1130 and last filtration region 1140.

In some embodiments, each of the filtration regions may comprise different size nanopores such that as a sample moves along the flow path 1101 through the series of filtration regions, particles of different sizes may be separated and collected. In some embodiments a sample is passed through filtration regions having sequentially smaller nanopores. Thus, in some embodiments the diameter of the nanopores of the second filtration region 1120 is different (typically smaller) than the diameter of the nanopores of the first filtration region 1110. Similarly, the diameter of the nanopores of each filtration region of the sequence of filtration regions may be different than the diameter of the nanopores of the other filtration regions. In some embodiments, the filtration regions 1110, 1120, 1130, and 1140 may be arranged from largest pore size to smallest pore size.

In some embodiments the sorting device comprises at least one separation layer 1150 that physically separates the filtration regions. In some embodiments the separation layer 1150 may serve not only to physically separate the filtration regions, but also to contain and direct the sample to the second filter 1120 by creating a flow path. The layer 1150 may be, for example, an elastomer layer. In some embodiments the layer 1105 is formed from PDMS.

The layer 1150 may be penetrable, for example by a needle. This may allow at least a portion of a sample that has passed through the previous filtration region to be removed during filtration. It may also allow addition of material to the space between filters, such as additional fluid or reagents. In some embodiments the separation layer 1150 is above and adjacent to the series of filters (first filter 1110, the second filter 1120, etc).

In some embodiments, the layer 1150 comprises at least one channel 1155, 1165. The channel 1155 may be used to add or remove material from a space (or the flow path) between two or more filtration regions. For example, particles can be removed that have passed through the filtration region prior to the channel. In some embodiments, the channel 1155 may approach an outer edge of the layer 1150 leaving a thin membrane (not shown). In some embodiments the membrane may be about 2 mm or less. In some embodiments, the membrane is configured to be punctured with a needle, such as a microfluidics needle. In other embodiments the spacer does not comprise a channel.

In some embodiments the sorting device comprises a second separation layer 1160. The second separation layer 1160 may be below and adjacent to the series of filtration regions (first filtration region 1110, the second filtration region 1120, etc). The second filtration regions may also comprise channels 1165 that may be used to add or remove material from a space (or the flow path) between two or more filtration regions.

In some embodiments, at least one of the separation layers 1150, 1160 may comprise a microfluidic device covering at least a portion of the series of filters before the first filtration region 1110. The microfluidic device may be, for example, configured to insert a carrier fluid and/or sample into the device. In some embodiments the separation layers comprise an elastomeric material such that a needle can be used to inject a sample into the space before the first filtration region 1110, such as into the flowpath 1101. The microfluidic device may be, for example, a molded elastomeric material such as PDMS.

In some embodiments, at least one of the separation layers 1150, 1160 may comprise a second microfluidic device covering at least a portion of the series of filtration regions after the final filtration region 1140. The second microfluidic device may be configured to collect the sample and particles that have passed through the filtration regions. In some embodiments, the sample that is collected in the second microfluidic device will comprise only particles that are smaller than any of the pores in the filtration regions.

Fabrication of Filters and Devices

Devices comprising nanopores can be formed by the methods disclosed herein. In some embodiments, nanopores can be formed on silicon substrates. In some embodiments nanopores preferably have a diameter less than about 50 nm, less than about 25 nm or even less than about 10 nm. For example, nanopores may be from about 0.1 to 1 nm, from about 1 to about 2 nm, from about 1 to about 3 nm, from about 1 to about 4 nm, from about 1 to about 5 nm, from about 1 to about 6 nm, from about 1 to about 7 nm in diameter. In some embodiments the nanopores may be about 1, 2, 3, 4, 5, 6, 7, 8, 9 or 10 nm in diameter. In some embodiments the nanopores may be less than about 1 nm in diameter, but sufficiently large to allow fluid passage. In some embodiments, multiple nanopores are formed on the substrate. In some embodiments all of the nanopores have approximately the same diameter. In other embodiments, nanopores of different diameters may be formed. Nanopores can be spaced between about 20-50 nm apart, thereby allowing fabrication of arrays of nanopores on a substrate. In some embodiments a single array is formed on a substrate. In other embodiments, multiple arrays may be formed on a single substrate. Each array of nanopores may comprise nanopores of a single size. In some embodiments, multiple arrays of nanopores are formed on a substrate, where individual arrays comprise nanopores of a size that is different from one or more other arrays on the substrate. That is, a single substrate may comprise one or more arrays of nanopores of a first size, and one or more arrays of nanopores of a second size, where the first size and second size are different. For example, a single substrate may comprise one or more arrays of nanopores of about 5 nm and one or more arrays of nanopores of about 2 nm. Microfluidic channels may be used in some embodiments to move a sample through various arrays on a single substrate. The substrates comprising nanopores may be used, for example, as filters for separating and sorting particles.

Briefly, a silicon substrate can be patterned to form nanopores having a desired size. First, a silicon substrate can be patterned and etched to leave raised silicon structures or nanopillars having a desired size and shape. The silicon nanopillars can then be oxidized in a controlled manner to form silicon dioxide on the outer area of the silicon nanopillars while leaving an un-oxidized portion of the nanopillar at the center of the structure having a desired size (an un-oxidized nanopillar core). A layer may optionally be deposited over the oxide, such as an aluminum oxide layer, for example to strengthen the substrate or to provide a layer to be used for a device or structure. Next, a portion of the silicon nanopillars can be removed using chemical or mechanical methods. A small portion of the silicon nanopillars may be left close to the surface of the substrate. Next, the remaining silicon portion of the silicon nanopillar (the silicon core) is selectively etched to create a nanopore having a desired size. A selective etch can also be used to etch a small internal cavity in the back side of the silicon substrate that is in fluid communication with a nanopore. Other layers, s can be deposited on portions of the device to achieve a filter with the desired properties. For example devices can be formed on the substrate, for example to make electrical measurements of materials moving through the nanopores. In other embodiments, physical barriers may be deposited to separate particular section of the substrate from other sections.

Figure 4:
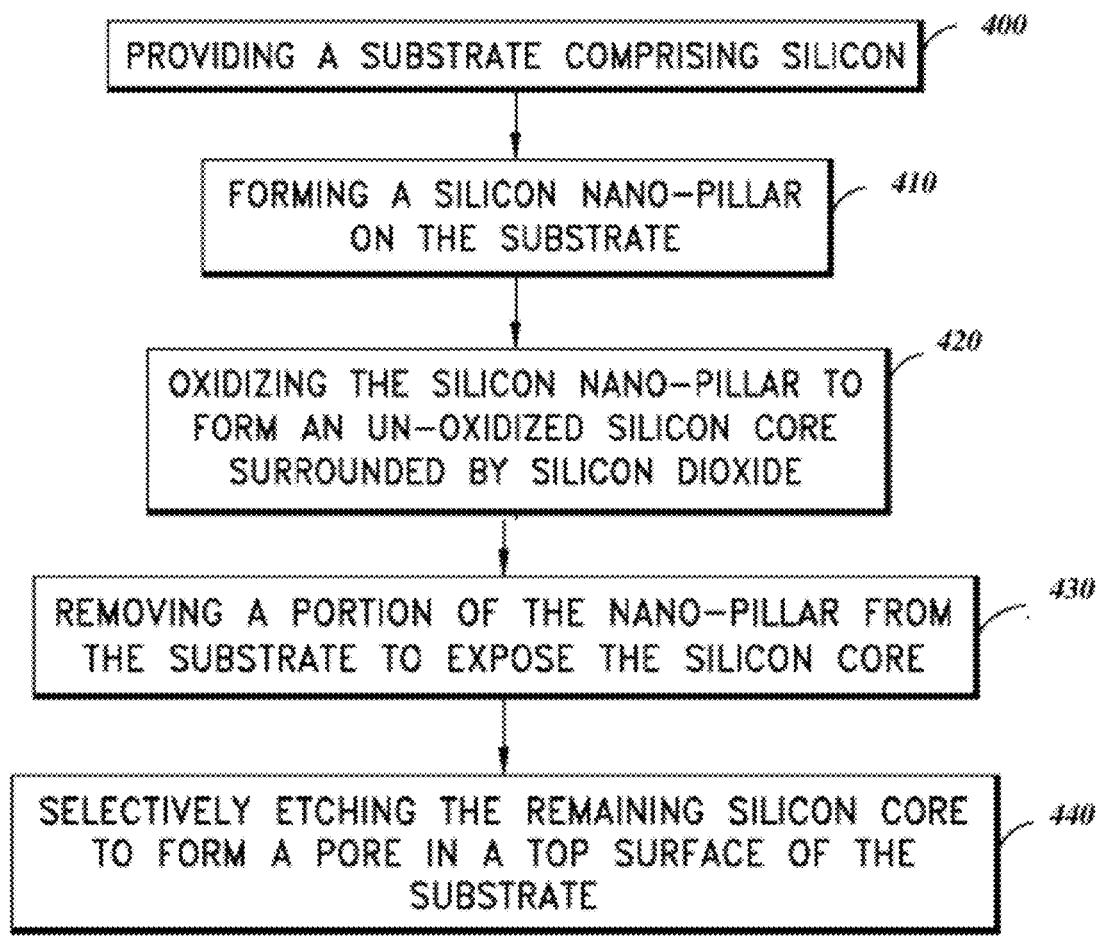
FIG. 4 shows a flow chart illustrating a method for forming a device for filtering nanoparticles.

FIG. 4 is a flow chart describing processes for producing a substrate comprising nanopores according to some embodiments. A substrate comprising silicon is provided 400. One or more nanopillars are formed 410 on the substrate, for example by masking and etching the silicon substrate.

Various methods can be used to pattern the substrate and form the nanopillars, including photo-lithography and electron beam lithography. In some embodiments, the silicon wafer is patterned on a polished surface using photo or electron beam lithography to form nano-scale spots. Preferably, the patterns have a diameter of about 20 nm to about 50 nm. Next, a hard mask can be placed on the patterned surface using a lift-off process. In some embodiments, reactive sputter deposited aluminum oxide can be used as a hard mask. Next an electron beam is used to remove the resist. Next, the silicon can be etched using plasma etching techniques commonly employed in the microelectronics industry. The hard mask is then selectively removed leaving high-aspect-ratio silicon nano-pillars.

The size of the nanopillars, their height, diameter, and spacing may be selected to provide nanopores of a desired size and pattern. In some embodiments, nanopillars are spaced at a distance equal to twice the diameter of the nanopillars or greater. In some embodiments the diameter of the nanopillar is from about 20 nm to about 50 nm. For example, for nanopillars with a diameter of about 50 nm, the center to center distance between adjacent nanopillars would be about 100 nm or greater.

In some embodiments the height of the nanopillars may be from about 200 nm to about 2.5 microns. In some embodiments, the height of the nanopillars is about 200 nm to about 250 nm. In some embodiments the diameter of the nanopillars is about 15 to about 100 nm or greater. In some embodiments, the diameter of the nanopillar is about 50 nm and the height is about 1 micron. Of course, nanopillars of other sizes can be used, depending on the process conditions and the size and arrangement of the nanopores to be formed.

In some embodiments, forming the nanopillars comprises: providing an area of resist to create a hole; depositing an oxide to the fill the hole; removing the resist; and etching the feature to create a nanopillar structure.

In some embodiments, the area of resist is circular. In some embodiments, the circular area of resist has a diameter as small as 30 nm.

In some embodiments, the area of resist is developed away to create a hole. The area of resist may be developed using lithographic techniques.

In some embodiments, a hard mask is provided on the surface of the substrate. In some embodiments, the hard mask may be patterned by means of a lift off process. For example, an oxide is deposited. The oxide may be sputtered. In some embodiments, the oxide is deposited using a reactive sputtering technique. In some embodiments, the holes are filled with the oxide. In some embodiments, an organic solvent is used to lift off the resist. In some embodiments, an electron beam is used to remove the resist leaving disks of alumina. These disks can be etched using a mixed mode "pseudo-Bosch" technique to create vertical nanopillars. In some embodiments, the oxide is an aluminum oxide.

In some embodiments, the disks are etched using plasma etching techniques. In some embodiments, the disks are etched using a mixed mode "pseudo Bosch" technique.

In some embodiments, the hard mask is then removed selectively. In some embodiments, removing the hard mask selectively leaves high-aspect-ratio silicon nanopillar structures, or nanopillars. In some embodiments, the nanopillar structures are around 1 to 100 nm in diameter and around 1 micron in height.

Figure 6:
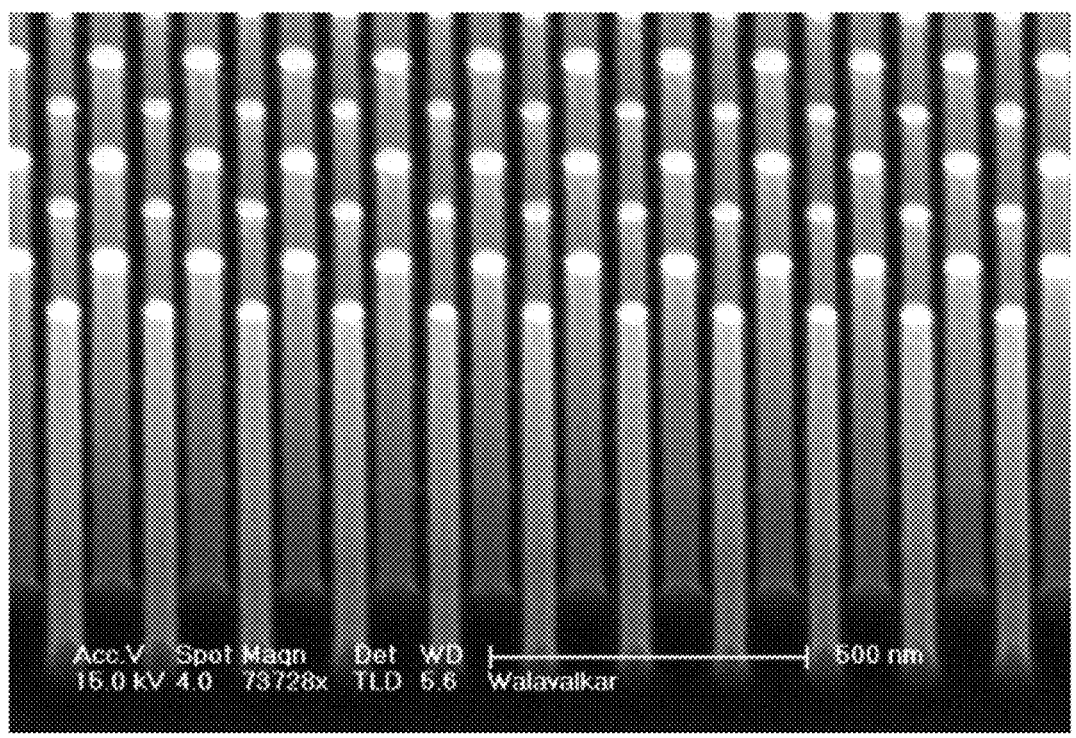
FIG. 6 shows an image of silicon nanopillars formed by the methods disclosed herein.

In some embodiments, an array of nanopillars is formed, as illustrated in FIG. 6.

The number, size, shape and pattern of the nanopillars can be controlled by the patterning of the mask and the extent of the etching process. In some embodiments the nanopillars are cylindrical and the mask is patterned accordingly. The number, size and arrangement of the nanopillars can be controlled by the masking and etching process. The diameter of the nanopillars may be determined based on the desired size of the nanopores to be formed and the oxidation process to be used in the next step. The height of the nanopillars can be controlled by controlling the extent of the etching of the substrate. In some embodiments the nanopillars can be made from materials other than silicon that can be treated to form a core that can be selectively etched.

The silicon nanopillar is oxidized 420 to form a nanopillar comprising a silicon dioxide shell and having a core of silicon. The oxidation may be controlled, for example by controlling temperature, pressure and the nature of the oxidant, in order to obtain a silicon core of a desired size. The size of the silicon core will determine the size of the nanopore formed.

Exposing the silicon nanopillars to an oxidizing environment forms silicon dioxide from the silicon in the nanopillar. It will be appreciated that thermal oxidation is common in the microfabrication of metal oxide semiconductor field effect transistors.

In some embodiments, the oxidation step can be carried out in an oxygen furnace. Oxidation of the silicon nanopillar forms silicon dioxide from the silicon on the outer area of the silicon nanopillar, as well as on the other exposed portions of the silicon substrate. The formation of silicon dioxide and expansion can cause strain to the silicon core of the oxidized pillars. The oxidation process can be self terminating because oxidation stops when the strain becomes too high. FIG. 5B shows a cross-section of a silicon substrate 500 with a silicon nanopillar 520 with a thin silicon dioxide layer 530 formed on the silicon substrate 500 and silicon nanopillar 520. In other embodiments silicon dioxide may only be formed from the silicon nanopillar 530 and not on the silicon substrate, for example by masking the substrate. FIG. 6 illustrates nanopillars before the oxidation step.

Figure 12:
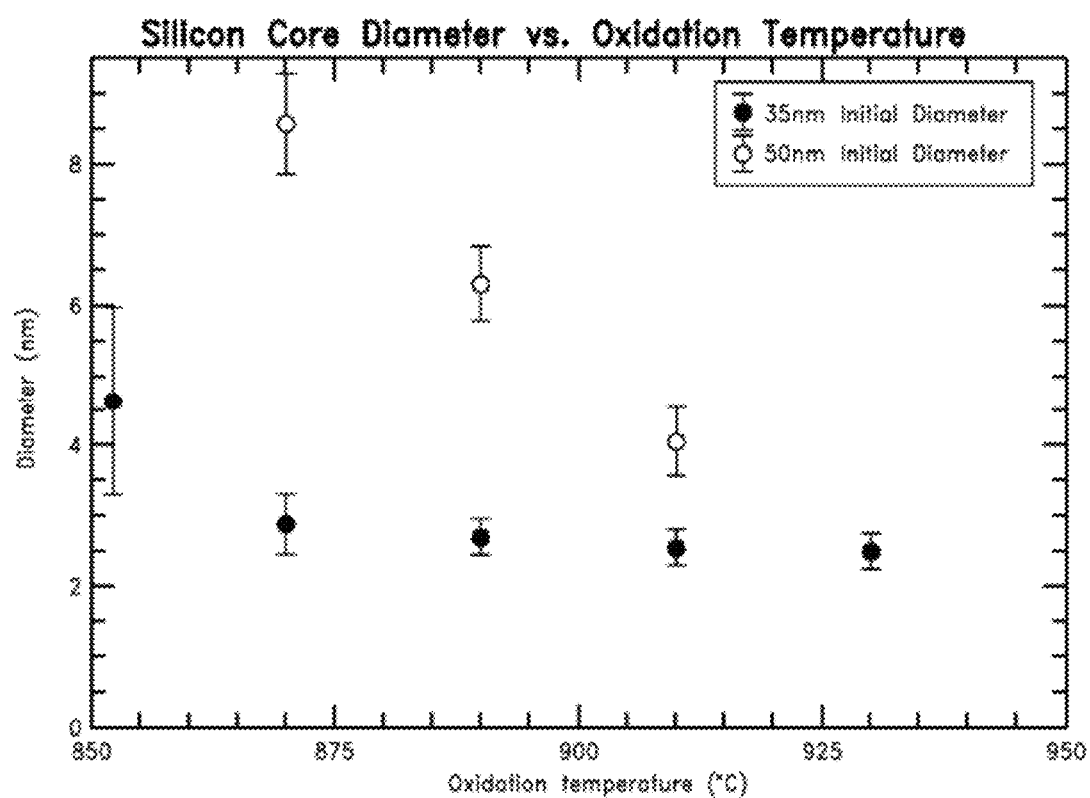
FIG. 12 illustrates a relationship between silicon core diameter and oxidation temperature.

In some embodiments, the oxidation conditions can be selected to achieve a desired amount of oxidation and, as a result, a desired width of the un-oxidized silicon at the core of the nanopillar. For example, the silicon nanopillar can be oxidized to a desired depth based on the oxygen furnace temperature. Applicants have discovered that the amount of silicon remaining at the core of the nanopillar is directly related to the temperature of the oxidation step and not oxidation time. In some embodiments, the nanopillar expand as they are oxidized. In some embodiments the temperature during the oxidation step is from about 800° C. to about 950° C. FIG. 12 is a graph illustrating the diameter of the un-oxidized silicon in the nano-pillar versus the oxidation temperature used during the oxidation step. FIG. 12 illustrates data for silicon nano-pillars having an initial diameter of about 35 nm and about 50 nm. The diameter of the silicon nanopillar (prior to oxidation) can be selected along with the oxidation temperature to achieve a desired nanopore size. In some embodiments the temperature during the oxidation step is above about 850° C., above about 900° C., above about 950° C., or above about 1000° C. The oxidation temperature can be selected to reliably form concentric silicon/silicon-dioxide cylinders (e.g. silicon cylinders or cores surrounded by an oxide sheath) having a silicon core with a desired width. In some embodiments, the silicon core of the nanopillar can have a width of less than about 10 nm. In some embodiments, the silicon core of the nanopillar can have a width of about 1 nm to about 5 nm after the oxidation step. In some embodiments, the silicon core of the nanopillar can have a width of about 1 nm to about 3 nm after the oxidation step. In some embodiments, the silicon core of the nanopillar after oxidation can have a width of less than or equal to about 1 nm, 2 nm, 3 nm, 4 nm, 5 nm, 6 nm, 7 nm, 8 nm, 9 nm, or 10 nm.

In some embodiments, a thin layer is deposited over the silicon dioxide (including the nanopillar). The thin layer may serve to strengthen the area of the substrate in which the nanopore is to be formed. For example, if silicon has been removed from the back side of the substrate under the nanopillar, a thin layer deposited over the oxide may strengthen the substrate during the etching of the silicon core and formation of the nanopore. In some embodiments the thin layer is an aluminum oxide layer. The aluminum oxide layer may be deposited after oxidation and prior to removing a portion of the nanopillar and etching the core.

Referring back to FIG. 4, a portion of the nanopillar is removed 430, thus exposing the silicon core. The portion of the nanopillar may be removed by physical or chemical methods. In some embodiments the nanopillars are physically broken to reveal the silicon core. In other embodiments a portion of the nanopillar is removed by a mechanical polishing or other mechanical and/or chemical method to expose the silicon core.

The silicon core of the nanopillar is then selectively etched 440, thereby forming a pore in a top surface of the substrate. In some embodiments the silicon core is etched from the top side of the substrate comprising the nanopillar. In other embodiments, the silicon substrate may be selectively etched from the back side to remove the silicon core.

In some embodiments the selective etching is continued until the pore goes through the entire thickness of the substrate.

The selective etching can remove silicon relative to silicon dioxide or the other materials present on the substrate. In some embodiments, a dry etch is used to selectively remove the silicon, such as etching with $XeF_2$ or other fluorine based etchants. In some embodiments a plasma or a wet etch, such as EDP (an aqueous solution of ethylene diamine and pyrocatechol), can be used for the selective etching. The etchant can be exposed to the front or top surface where the nanopillars were formed or the back of the substrate. In some embodiments, the etching can result in the formation of hollow silicon dioxide shells with the interior defining a nanopore. The etching conditions, such as time, temperature, and etchant can be selected to etch the nanopore and a portion of the silicon substrate underneath the nanopillar to create an internal cavity in the silicon substrate with a desired volume. In some embodiments, an internal cavity can be etched in the silicon substrate from the back of the substrate, such that the internal cavity is in fluid communication with the nanopore. The etching of the backside to form the internal cavity can be carried out after forming the nanopore. However, in other embodiments the etching is carried out after oxidation, but prior to etching the silicon core of the nanopillar. In some embodiments the silicon remaining on the back side of the substrate is completely removed.

In some embodiments the remaining portion of the nanopillar is etched back to the level of the silicon substrate.

In some embodiments, an oxide layer is provided on the back side of the substrate. For example an aluminum oxide layer can be deposited on the back side of the substrate. In other embodiments the oxide layer is formed from the silicon in the substrate itself. After forming an oxide layer on the back side of the substrate, if desired, a hole can be patterned into the oxide layer using lithographic techniques. The hole may be patterned directly below a nanopillar. In some embodiments, the hole is square. The substrate can then be etched through the hole on the backside. In some embodiments, the hole is etched into the substrate using a first etch to form an internal cavity. In some embodiments, the first etch is an anisotropic cryogenic silicon etch.

The size of the nanopore is preferably sized to allow molecules of a desired size to pass through, while retaining larger molecules. The size of the nanopore is dependent on the size of the un-oxidized silicon core remaining in the nanopillar after oxidation. In some embodiments, the nanopore has a diameter or width of about 5 nm or less. In some embodiments, the diameter or width of the pore is from about 1 nm to about 5 nm or about 1 nm to about 2 nm. In some embodiments, the nano-pore has a width of about 1 nm, 2 nm, 3 nm, 4 nm, 5 nm, 6 nm, 7 nm, 8 nm, 9 nm, or 10 nm.

Additional processing steps may be carried out, as necessary to obtain the desired features on the substrate.

Figure 5A:
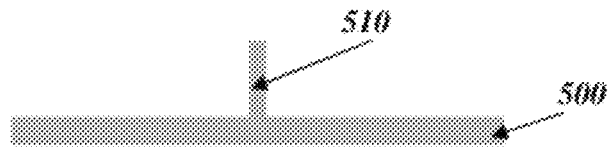
FIG. 5A-5E illustrates cross-sections of a substrate during various steps for forming a device for separating particles.
Figure 5B:
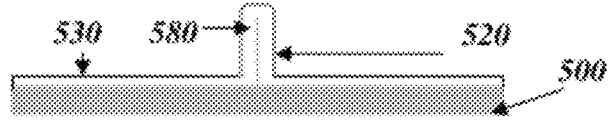

FIGS. 5A-5E illustrates a process of making nanopores in a silicon substrate according to some embodiments. First, a silicon substrate 500 is patterned and etched to leave raised silicon structures or nanopillars 510 having a desired size and shape (FIG. 5A). Typically, the nanopillars are cylindrical. The diameter of the nanopillars will be determined, in part, by the desired size of the nanopores to be formed. In some embodiments the nanopillars are about 35 nm in diameter. In some embodiments the nanopillars are about 50 nm in diameter. In some embodiments the nanopillars can be etched to about 15 nm. In some embodiments the nanopillars are about 200 nm in height. As discussed below, each nanopillar corresponds to a single nanopore. One or more nanopillars may be formed at a time by the appropriate masking and etching. When one or more arrays of nanopores are to be formed, nanopillars corresponding to each nanopore are formed.

The silicon pillars are oxidized in a controlled manner to form silicon dioxide 520 on the outer area of the silicon nanopillars while leaving an un-oxidized portion 530 of the non-pillar at the center of the structure (FIG. 5B). The unoxidized portion may be referred to as the silicon core 580. The oxidation process is controlled to produce a silicon core of the desired diameter, as the size of the silicon core will determine the size of the nanopore corresponding to the pillar. For example, if a 2 nm nanopore is to be formed, oxidation is carried out under conditions such that a 2 nm core of unoxidized silicon remains at the center of the nanopillar. A small portion of the silicon nanopillars may be left close to the surface of the substrate.

In some embodiments, a layer is deposited on the substrate after oxidation and prior to removing a portion of the nanopillars (not shown). For example, an aluminum oxide layer can be deposited over the silicon dioxide. The layer may server to strengthen the silicon dioxide layer during subsequent processing.

Figure 5C:
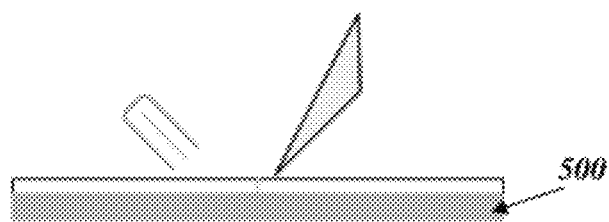
Figure 5D:
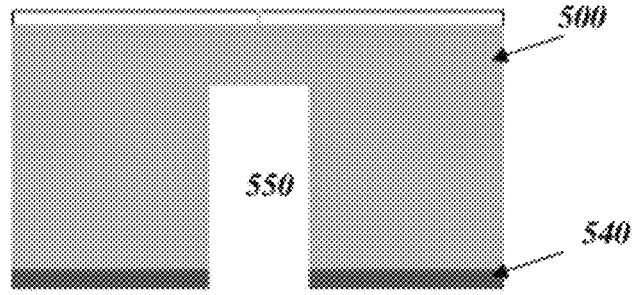

Next, a portion of the silicon nanopillars can be removed using chemical or mechanical methods (FIG. 5C). A cavity 550 may optionally be etched into the silicon substrate underneath the nanopillar, such that it is in fluid communication with the nanopillar (FIG. 5D). A mask 540 may be deposited and patterned on the reverse side of the substrate from the pillar. The silicon may be etched back to create the cavity 550 underlying the nanopillar. In some embodiments, the silicon substrate is etched away completely, leaving the silicon core in a silicon oxide substrate.

Figure 5E:
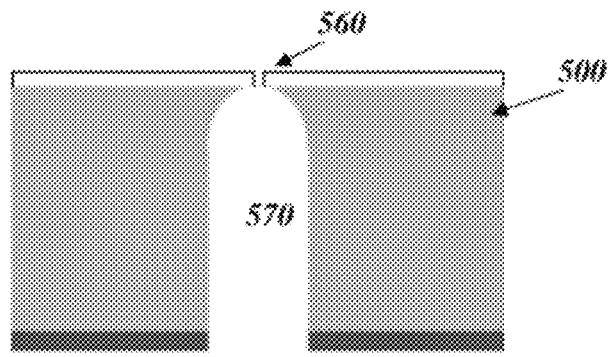

The silicon core of the nanopillar is selectively etched through the substrate to create a nanopore 560 having a desired size (FIG. 5E). A selective etch can also form a small internal cavity 570 in the silicon substrate that is in fluid communication with the nanopore.

Selective etching of the nanopillar forms a nanopore and, optionally, an internal cavity in the substrate. The etchant can be exposed to the front polished surface where the nanopillars were formed or to the back of the substrate. In some embodiments, the etching can result in the formation of hollow silicon dioxide shells with the interior defining a nanopore. In some embodiments, an internal cavity can be etched in the silicon substrate that is in fluid communication with the nanopore. The etching conditions, such as time, temperature, and etchant can be selected to etch the nanopore and a portion of the silicon substrate to create an internal cavity in the silicon substrate with a desired volume.

In some embodiments the nanopillars can be made from materials other than silicon that can be selectively etched. For example, the nanopillars can be made from germanium, tungsten, titanium, or III-V materials, such as Gallium Aresenide, Indium Arsenide, Aluminum Arsenide, Gallium Nitride, Indium Nitride, Aluminum Nitride, and any alloys of the above listed materials[

The size of the nanopore is preferably sized to allow a nanoparticle of a desired size to pass through. The size of the nanopore is dependent on the size of the un-oxidized silicon remaining in the nanopillar after oxidation. In some embodiments, the nanopore has a diameter or width of about 5 nm or less. In some embodiments, the diameter or width of the pore is from about 1 nm to about 5 nm or about 1 nm to about 2 nm.

In some embodiments, one or more arrays of nanopillars is formed on the substrate in order to create one or more arrays of nanopores. In some embodiments, each nanopillar is about 50 nm or more from adjacent nanopillars, if any. In some embodiments, the distance between nanopores of the ultimate array can be about 300 nm to 500 nm from center to center. In some embodiments, the distance between nanopores of an array can be about 500 nm to 1 micron from center to center. In some embodiments, the distance between nanopores of the array can be about 150 nm from center to center. The exact distances can be determined based on the use of the substrate comprising the nanopores and can be formed using the appropriate patterning techniques. As mentioned above, in some embodiments, the distance between the nanopores (center to center) is twice the diameter or greater than the diameter of the nanopillars from which they were formed. For example, the distance between nanopores (center to center) may be about 100 nm when formed from nanopillars having a diameter of about 50 nm.

In some embodiments, the above-described processes can be used to form an array of nanopores of a particular size on one portion of a substrate while a second portion of the substrate remains protected. Subsequently, the second portion of the substrate may be patterned while protecting the first portion, such that a second array of nanopores of a different size is formed on the second portion of the substrate. Additional arrays may be formed in this way, such that a substrate may contain 1, 2, 3, 4, 5, 6, 7, 8, 9, 10 or more arrays of nanopores. In some embodiments each array may comprise different sized nanopores from at least one other array. In some embodiments, each array comprises nanopores of a different size from each other array on the same substrate.

Multiple arrays of nanopores are illustrated in the photomicrograph in FIG. 7. Individual nanopores are illustrated in FIGS. 8 and 9.

Once formed, substrates comprising one or more nanopores can be used in any of a wide variety of applications. In some applications they are used as filters, to separate particles of a particular size. Two or more filters may be stacked to form a filtration device as described herein, or used by themselves. In some embodiments, two or more filtration regions, each comprising a particular size of nanopore, may be formed on a single substrate to form an array of filtration devices as described herein. In other embodiments, a series of two or more filters and/or filtration regions may be formed on a single substrate to form a sorting device as described herein.

Methods of Isolating and Sorting Particles

Methods are disclosed herein for isolating and/or sorting nanoparticles in a sample. The methods disclosed herein can be used, for example, to separate particles by size. For example, metal-based, lipid-based, polymer-based or biological particles may be separated by the methods and devices disclosed herein. In some embodiments, biological particles to be separated may include but are not limited to exosomes, vesicles, proteins, viruses, and DNA. In other embodiments, gold nanoparticles may be separated by the methods and devices disclosed herein.

In some embodiments, a method of isolating particles comprises flowing a sample comprising at least one particle through a first filter, wherein the first filter comprises two or more nanopores. In some embodiments the filter comprises nanopores in a silicon and/or silicon dioxide substrate. The nanopores are sized to allow particles of a desired size to pass through, while particles larger than the nanopores do not. In some embodiments the two or more nanopores each have a diameter of about 5 nm or less, about 4 nm or less, about 3 nm or less or about 2 nm or less.

For example, in some embodiments a mixture of nanoparticles, such as gold nanoparticles, are sorted by size. The mixture of nanoparticles may comprise nanoparticles of known sizes, a known range of sizes, such as 5 to 100 nm, or unknown sizes. The mixture is passed through a series of arrays of nanopores from smallest to largest such that the nanopores are separated by size. For example, the mixture may be passed through a series of arrays of nanopores with each array being 10 nm larger than the previous array, such that the nanoparticles are separated into sizes by 10 nm increments. Of course the particular size of the nanopore arrays may be selected based on particular circumstances and the desired level of separation.

In some embodiments the sample comprising the nanoparticles is a fluid. In some embodiments the sample is a liquid. In some embodiments, the sample is not a liquid. In some embodiments, the sample comprises predominantly nanoparticles.

Samples comprising particles of different sizes may be sorted and the sorted particles collected. A stack of two or more filters may be assembled, for example as disclosed above, and used to sort particles in a sample based on size. A sample carrying particles of two or more sizes can be filtered through two or more filters, each having nanopores of decreasing diameter. For example, a sample comprising known to or suspected of comprising nanoparticles of 2 and 5 nanometers could be passed through a first filter comprising nanopores of 6 nm and a second filter comprising nanopores of 3 nm in order to separate the 2 nm particles from the 5 nm particles. Particles of 5 nm would pass through the first filter but not the second, and thus could be recovered from a space between the first filter and the second, while the particles of 2 nm would pass through both filters and could thus be collected from the sample that passed through the second filter.

In some embodiments, a sample comprising multiple nanoparticles of unknown sizes is passed through a series of filters in order to separate and collect particles of various sizes. For example, the sample may be passed through a 10 nm filter, an 8 nm filter, a 6 nm filter, a 4 nm filter and a 2 nm filter. The filters may be arranged such that the sample passes sequentially through the filters. After passing through each filter, a portion of the sample can be removed. In this way, particles of between 2 nm and 4 nm can be collected, particles between 4 nm and 6 nm can be collected, particles between 6 nm and 8 nm can be collected and particles between 8 nm and 10 nm can be collected. Of course, the sizes and numbers of the filters can be selected to achieve the desired separation of particles.

In some embodiments, a method of sorting biological particles comprises flowing a sample comprising at least one particle through a filter or stack of filters. The flow of the sample through the stack may be aided by utilizing a pressurized fluid. For example, the sample may be mixed with or injected into a pressurized fluid and applied to a filter. In other embodiments the sample is applied to a filter and the filter is subsequently or simultaneously contacted with a pressurized fluid to aid movement of the sample across the filter. In other embodiments a pressurized fluid is continuously applied to one or more filters.

In some embodiments, a first carrier fluid comprising at least one nanoparticle is provided. A first filter is provided with at least one nanopore of diameter larger than the size of the nanoparticle. Preferably the filter comprises at least two nanopores of the same diameter. A second filter is provided, comprising at least one nanopore smaller than the diameter of the nanoparticle. Preferably the second filter comprises at least two nanopores of this size. In some embodiments the first and/or second filters comprise 10, 100, 1,000, 10,000, 100,000 or more nanopores. An insert or spacer layer may be disposed between the first filter and the second filter to provide a flow path from the first filter to the second filter. The spacer layer may comprise, for example, a molded elastomer comprising a hole and a channel as described above. A second carrier fluid is provided in the flow path between the first and second filters, wherein the first carrier fluid is at a higher pressure than the second carrier fluid, such that the nanoparticle passes through the first filter but not the second. Pressure is removed between the filters and a washing fluid is flowed into the space between the first and second filters such that particles on the second filter can be extracted, for example with the aid of a needle.

In some embodiments a sample may be introduced to the top of a device comprising multiple filters and sequentially filtered through each of the filters in the device, where sequential filters comprise nanopores of decreasing diameter. In some embodiments, the sample is introduced through a microfluidic device configured to insert a needle with the sample. Nanoparticles that collect at each filter (because they are too big to pass through the nanopores of that filter), may be collected. For example, microfluidic needles can be inserted into the space separating the various filter layers in order to withdraw nanoparticles that collect at each filter stage. During the filtration portion of operation, a carrier solution devoid of sample particulates may be provided into the flow path to aid flow of the sample through the filters. A carrier solution may also be used to remove particles that collect at one or more of the filters. In some embodiments, the sample carrying the particles to be filtered will be introduced into a top microfluidic channel at a higher pressure than the fluid being flowed into the flow path between filters, thus forcing the particles through each filter and along the flow path towards the filter beneath. In some embodiments, no pressure is applied to the a bottom microfluidic channel underneath the last filter, thereby making the path of highest pressure difference towards the bottom. In some embodiments, when the sample to be filtered is exhausted, the pressure to the flow path between the filters can be turned off and a carrier fluid can be introduced to move the sorted particles into an area where they can be collected.

The decreased size of the individual devices and pores can allow for small volumes of liquid or sample to be sorted efficiently.

EXAMPLES

Example 1

Fabricating Nanopores

A hard mask of aluminum oxide was sputtered onto a silicon substrate and patterned to form nanodisks having a diameter of about 35 nm spaced evenly apart. A mixture of $SF_6/C_4F_8$ was used to etch the silicon substrate around the hard mask, thereby forming a number of silicon nanopillars with diameters of about 35 nm. FIG. 6 shows silicon nanopillars after removal of the hard mask. After removing the aluminum oxide hard mask using hydrofluoric acid, the nanopillars were oxidized in a furnace at a temperature of above 850° C. The methods in this example resulted in an un-oxidized silicon nanopillar core having a diameter of about 2 nm. Mechanical polishing was performed to remove portions of the nanopillars in order to expose the un-oxidized silicon core at the base of the nanopillars. $XeF_2$ was used to etch the remaining un-oxidized silicon cores to form nanopores with a diameter of about 2 nm. $XeF_2$ was also used to etch a portion of the backside of the substrate to form internal cavities in fluid communication with the nanopores.

Example 2

Fabricating Nanopores

A silicon substrate is patterned and etched to form nanopillars having a diameter of about 100 nm. The etching is performed as described in M D Henry et al 2009 *Nanotechnology* 20 255305. The nanopillars are oxidized at 900 C for 5 hours to form silicon dioxide nanopillars comprising about 20 nm silicon cores. Aluminum oxide is deposited over the silicon dioxide layer to strengthen the membrane. Nanopillars are snapped off with a q-tip. A hole is patterned on the back-side of the 400 micron thick wafer. A cryogenic silicon etch is performed to go about 250 microns into the wafer, following the masked hole. XeF2 is used to etch the cores of silicon out of the nanopillars, thereby forming nanopores in the substrate.

Example 3

Forming a Microfluidic Device to Sort Particles

Starting with bare silicon, PMMA (poly methylmethacrylate) was spun onto a wafer and baked at 180 C to drive off the solvents suspending the PMMA. The PMMA was irradiated with an electron beam using an electron beam pattern generator (EBPG) at 100 kV and 1.5 nanoAmp beam current. The locations where the electron beam sliced through the PMMA were dissolved away in a 1:3 mixture of Methyl-Isobutyl-Ketone (MIBK) and Isopropanol thus defining an array of 150 nm holes and a separate array of 50 nm holes in the PMMA. Aluminum oxide was sputter deposited onto the sample and into the holes using a DC magnetron sputtering system at 400 W with a 1:5 mixture of O2:Ar process gas chemistry. The chip was then placed in chloroform to dissolve away the PMMA. This removed the aluminum oxide sitting on the PMMA but left the alumina that had been deposited into the circular holes defined in the PMMA. Thus, a series of 150 and 50 nm disks of aluminum oxide were formed.

These samples were etched in an inductively coupled plasma-reactive ion etcher (ICP-RIE) with a gas chemistry of SF6 and C4F8, thereby creating nanopillars. The alumina mask was removed with hydrofluoric acid and the samples were oxidized at 850° C. for 1 hour forming a 15 nm layer of oxide on the surface and decreasing the diameter of the pillars slightly. Then, 100 nm of Aluminum oxide was sputtered onto the top surface of the chip to lend structural support to the membrane and the pillars were broken off with a q-tip.

Next, two large (400 micron) square holes were defined on the backside of the chip using photolithography. These holes were etched through the wafer using a combination of Cryogenic silicon etching and XeF$_2$ etching. Once the etch reached the silicon dioxide layer on the front-side of the wafer the XeF$_2$ etched out the core of the oxidized nanopillars leaving a nanopore. Next, microfluidic channels were placed on top and bottom to allow for fluid to flow up through the 150 nm holes and down through the 50 nm holes. Any particles between 150 nm and 50 nm would be trapped on the microfluidic channel on the top-side of the chip. The use of 150 and 50 nm was specific to the size of gold particles to be sorted, as described below.

Example 4

Sorting Gold Nanoparticles

The microfluidic device described in Example 3 was used to separate nanoparticles of gold. A sample comprising three sizes of gold particles was applied to the device and passed through the 150 nm and 50 nm arrays of nanopores. The three sizes of particles were such that the largest particles would not pass through the 150 nm nanopore array, the middle sized particles would not pass through the 50 nm nanopore array and the smallest particles would pass through both arrays. Particles were collected at the 150 nm array of nanopores and at the 50 nm array of nanopores. In addition, particles that were small enough to pass through both arrays were collected. In this way, the particles were sorted by size.

Example 5

Biological Nanoparticles

A hard mask is applied to a silicon substrate in a desired pattern. The silicon substrate is then etched to create a raised pattern in the shape of the hard mask. Next, the hard mask is removed to leave raised silicon structures on the substrate. The silicon substrate and raised silicon structures are then oxidized such that a silicon core having a desired width remain within the structures (nanopillars) after oxidation. Next, a portion of the nanopillars is removed to expose the silicon core. The remaining un-oxidized silicon nano-pillar core is etched to create a nano-pore having a desired diameter.

At least two arrays of nanopores are formed on the substrate as described above. Next, microfluidic channels are placed on top and bottom to allow for fluid to flow up through the first set of nanopores and down through the second set of nanopores. A sample of biological particles is applied to the device. Any particles between diameters of the first and second nanopores are trapped on the microfluidic channel on the top-side of the chip.

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

What is claimed is:

1. A filter comprising two or more nanopores, wherein each of the nanopores has a diameter of about 5 nm or less, wherein the filter comprises a layer consisting essentially of silicon dioxide and wherein the nanopores are present in the layer consisting essentially of silicon dioxide and wherein each of the nanopores has the diameter across an entire thickness of the layer.

2. The filter of claim 1, wherein each of the nanopores has a diameter of about 2 nm or less.

3. The filter of claim 1, wherein the filter comprises ten or more nanopores.

4. The filter of claim 1, wherein the filter comprises 1000 or more nanopores.

5. The filter of claim 1, wherein the two or more nanopores comprise a first array.

6. The filter of claim 1, additionally comprising a second array of nanopores, wherein each of the nanopores in the second array has a different diameter from the nanopores in the first array.

7. The filter of claim 5, wherein the nanopores of the array are about 50 nm center to center from adjacent nanopores.

8. A device for sorting particles, said device comprising:
a first filter comprising two or more nanopores in a first layer consisting essentially of silicon dioxide, each of the two or more nanopores having a first diameter, wherein each of the two or more nanopores in the first layer has the first diameter across an entire thickness of the first layer;
a second filter comprising two or more nanopores in a second layer consisting essentially of silicon dioxide, each of the two or more nanopores having a second diameter, wherein each of the two or more nanopores in the second layer has the second diameter across an entire thickness of the second layer, wherein the first diameter is different than the second diameter, and wherein the first diameter or the second diameter is about 5 nm or less.

9. The device of claim 8, wherein the first filter and the second filter are separated by a spacer layer.

10. The device of claim 9, wherein the spacer layer comprises an elastomer.

11. The device of claim 9, wherein the spacer layer comprises a hole and a channel, wherein the hole is arranged such that fluid passing through the nanopores of the first filter passes through hole and contacts the second filter.

12. The device of claim 11, wherein the channel has a width of about 200 microns.

13. The device of claim 11, wherein a first end of the channel connects to the hole and a second end of the channel approaches an outer edge of the spacer layer.

14. The device of claim 8, wherein the first diameter or second diameter is about 2 nm or less.

15. The device of claim 8 wherein the first diameter is greater than the second diameter.

16. The device of claim 8, further comprising a first microfluidic device configured to direct a sample to the first filter.

17. The device of claim 8, further comprising a second microfluidic device configured to collect a sample that has passed through the first and second filters.

18. A method of separating particles from a sample comprising:
flowing the sample comprising the particles through a first filter, wherein the first filter comprises a layer consisting essentially of silicon dioxide and two or more nanopores with a diameter smaller than the particles to be separated from the sample, and wherein the nanopores are present in the layer consisting essentially of silicon dioxide and have a diameter less than about 10 nm, and wherein each of the nanopores has the diameter across an entire thickness of the layer.

19. The method of claim 18, wherein the nanopores have a diameter of about 5 nm or less.

20. The method of claim 18, wherein the nanopores have a diameter of about 2 nm or less.

21. A method of sorting nanoparticles by size, said method comprising:
flowing a sample comprising two or more nanoparticles through a first filter, wherein the first filter comprises two or more nanopores in a first layer consisting essentially of silicon dioxide, each nanopore having a first diameter, and wherein each of the two or more nanopores in the first layer has the first diameter across an entire thickness of the first layer; and
subsequently flowing the sample through a second filter, wherein the second filter comprises two or more nanopores in a second layer consisting essentially of silicon dioxide, each nanopore having a second diameter smaller than the first diameter, wherein the second diameter is equal to or less than about 5 nm, and wherein each of the two or more nanopores in the second layer has the second diameter across an entire thickness of the second layer,
wherein the two or more nanoparticles comprise at least one first nanoparticle with a third diameter larger than the first diameter and at least one second nanoparticle with a fourth diameter larger than the second diameter.

22. The method of claim 21, wherein the second diameter is equal to or less than about 2 nm.

23. The method of claim 21, wherein at least one of the nanoparticles is a biological particle.

24. The method of claim 20, wherein the biological particle is a cellular component.

25. The method of claim 21, wherein the first and second filters are separated by at least one spacer layer.

26. The method of claim 21, further comprising collecting a portion of the sample after the sample passes through the first filter.

27. The method of claim 21, further comprising collecting a portion of the sample after the sample passes through the second filter.

28. The method of claim 21, wherein the first filter is a first filtration region on a substrate and the second filter is a second filtration region on the substrate.

* * * * *